4,964,725
Date: Oct. 23, 1990
Inventors: Goldovsky et al.

CORRELATIONAL GAS ANALYZER

Inventors: Viktor L. Goldovsky, ulitsa Shopena, 18, kv. 6; Viktor I. Stetsovich, ulitsa Donskaya, 33; Andrei J. Zayats, ulitsa Gagarina, 27a, all of Uzhgorod, U.S.S.R.

[21] Appl. No.: 339,498

[22] Filed: Apr. 17, 1989

[51] Int. Cl.$^5$ .............................. G01J 3/06; G01J 3/32; G01N 21/35
[52] U.S. Cl. .................................. 356/308; 250/339; 356/328
[58] Field of Search ................ 356/308, 310, 326, 328, 356/334; 250/339

[56] References Cited

U.S. PATENT DOCUMENTS

| | | | |
|---|---|---|---|
| 2,849,618 | 8/1958 | Smith | 250/339 |
| 3,700,331 | 10/1972 | White | 356/308 |

OTHER PUBLICATIONS

Prikladnaya infrakrasnaya spektroskipiya Ed. D. Kendall, Moscos, MIR Publishers 1970.
R. Haulet, C. Vasseur "Teledetection des pollutants gaseoux de l'atmospher" Bull, inform. sci, et techn, 19/8, 230/231 p. 59.

*Primary Examiner*—Vincent P. McGraw
*Attorney, Agent, or Firm*—Lilling and Lilling

[57] ABSTRACT

The correlational gas analyzer comprises a light source passed through the gas under study, which features a quasiperiodic pattern of the specified spectral band, and an optical system with sequentially positioned along the optical path condensor, input slit iris, dispersing means to decomposed the specified spectral band of the gas under study, and rotatably mounted output slit iris configures as a disc with a plurality of slits, uniformly distributed along its circumference and equidistant from the disc center. The spacing between the centers of adjacent slits is approximately equal to the scan length of the specified spectral band of the gas under study. The output slit iris scans the specified spectral band of the gas under study across a photoreceiver, the output signal whereof drives two electric signal amplifiers. One of the amplifiers is designed as a tuned amplifier, with the resonant frequency thereof defined by a preset relation between the disc rotation speed, the number of maxima or minima in the specified spectral band, and the number of slits in the disc.

4 Claims, 2 Drawing Sheets

CORRELATIONAL GAS ANALYZER

FIELD OF THE INVENTION

This invention relates to optical instrumentation and more specifically to correlational gas analyzers.

This invention can be used in chemical industry to analyze compositions of gas mixtures, in microelectronics to monitor the environment in the work zone, in metallurgy and in other industries. This invention and also be successfully used in environment control to monitor pollution by exhaust gases, such as $SO_2$, $NO_2$, $NO$, $NH_3$, etc.

BACKGROUND OF THE INVENTION

Currently, most high selectivity gas analyzers are based on correlational spectroscopy, wherein gas concentration is determined from characteristic features of the spectrum of the gas under study, such as quasiperiodic absorption or transmission spectra. These gas analyzers should be able to perform multicomponent analysis of the gas under study without unduly complicating their design and should also feature simplicity of conversion to measurement of the content of another gas component in the mixture.

Known in the art is a correlational gas analyzer ("Prikladnaya infrakrasnaya spektroskopiya", Ed. D. Kendall, Moscow, MIR Publishers, 1970), comprising a light source and sequentially positioned along the beam path interference filter to select the specified spectral band of the gas under study, a modulator, two cells with one cell filled with the gas under study and the second cell filled with a gas that does not absorb radiation in the specified spectral band, a photoreceiver, and a recorder.

After passing through the cell filled with the gas under study the light beam does not contain spectral components corresponding to absorption lines, while at the output of the other cell it contains all spectral components of the spectral band selected for gas analysis. The photoreceiver generates a signal proportional to light attenuation in the gas under analysis due to absorption and this signal allows detection and assessment of concentration of the gas under study positioned in the beam path between the light source and the photoreceiver.

This known in the art gas analyzer features poor accuracy and low reproducibility of measurement results due to absorption of the gas under study and to its leakage out of the cell. In case of corrosive gases, such as $H_2S$ or $SO_2$, and unstable gases, such as $NO_2$, the use of this gas analyzer is hampered by the necessity to maintain constant temperature and humidity.

Also known in the art is a correlational gas analyzer (R. Haulet, C. Vavasseur "Teledetection des pollutants gaseoux de l'atmosphere" Bull. inform. sci. ez techn., 1978, 230/231, p.59) comprising a light source with the beam thereof passing through the gas under study which features a quasiperiodic spectrum pattern in the specified spectral band, and through an optical system comprising sequentially positioned along the optical path condensor, input slit iris, specified spectral band dispersing element, and rotatably mounted output slit iris configured as a disc with a group of slits for scanning the specified spectral band of the gas under study across the photoreceiver, with the output thereof connected to a recorder via an electric signal amplifier.

In this known in the art correlational gas analyzer a concave grating is used as the specified spectral band dispersing element, while the slits in the disc are shaped as arcs and positioned to coincide with the maxima and minima in the absorption of the gas under study in the focal plane of the concave grating.

The light passed through the gas under analysis is decomposed into a spectrum by the concave grating and then passed via the slits of the rotating disc. Thus the spectral band of the gas under study is discretely scanned across the photoreceiver, the modulation depth of the light beam being proportional to the difference in intensity of corresponding light transmission and absorption bands in the spectral band of the gas under study and dependent therefore on the content of this gas in the volume.

The optical system of this known in the art gas analyzer is complicated and therefore hard to manufacture, as is disc alignment, because its slits have to be precisely aligned to the maxima and minima of absorption in the gas under study spectrum, this critically affecting the measurement accuracy and leads to low measurement result reproducibility. Conversion to measurements of another gas component of the multicomponent gas mixture requires replacement of the disc with another, with appropriate slits, and its realignment in the optical system.

SUMMARY OF THE INVENTION

The objective of this invention is to provide a correlational gas analyzer allowing analysis of multicomponent gas mixtures without replacements of the disc in the optical system.

This is achieved by that in a correlational gas analyzer comprising a light source, the radiation beam whereof passes through the gas under study with a quasiperiodis pattern of the specified spectral band, and an optical system comprising sequentiall positioned along the optical path condensor, input slit iris, a dispersing means for decomposing the specified spectral band of the gas under study, and a rotatably mounted output slit iris with a group of slits to scan the specified spectral band of the gas under study across a photoreceiver, with the output thereof connected to a recorder via an electric signal amplifier, according to this invention the slits of the disc are uniformly spaced along the disc circumference and equidistantly spaced relative to the disc centre, with the spacing between centres of adjacent slits approximately equal to the scan length of the specified spectral band of the gas under study in the scan plane, and the gas analyzer further comprising an auxiliary electric signal amplifier with input connected to the photoreceiver output, and corrector unit with inputs connected to the outputs of the master and auxiliary electric signal amplifiers and with output connected to the recorder, wherein the master electric signal amplifier is a tuned amplifier with the resonant frequency defined by the preset relation between the disc rotation speed, the number of maxima or minima in the specified spectral band of the gas under study, and the number of slits in the disc.

It is preferrable that the resonant frequency of the master tuned electric signal amplifier be defined from the relation: $f_1 = (\Delta\lambda/\delta\lambda)/NK$, where $\Delta\lambda$ is the specified spectral band of the gas under study, $\delta\lambda$ is the period of the pattern of the specified spectral band of the gas under study, $N$ is the speed of disc rotation, and $K$ is the number of slits in the disc.

It is useful that the auxiliary electric signal amplifier be a tuned amplifier, with the resonent frequency thereof defined by the disc rotation speed and number of slits in the disc.

The correlational gas analyzer of the invention allows studies of gas components of a multicomponent gas mixture without replacements of the disc in the optical system, this essentially improving measurement accuracy by reducing errors due to misalignment of the disc in the optical system.

Manufacturing the disc with uniformly spaced along its circumference slits is easily acomplished technologically and is readily adaptable to streamlined production.

Designing the correlational gas analyzer circuitry with two tuned amplifiers and a corrector unit provides analyzer immunity to various interference, thus improving measurement accuracy.

BRIEF DESCRIPTION OF ACCOMPANYING DRAWINGS

These and other objectives of this invention will become apparent from the following description of its embodiments and accompanying drawings, wherein:

FIG. 1 schematically shows the correlational gas analyzer with a sectional view of the optical system, according to the invention;

FIG. 2 shows the disc with a group of slits and transmission spectra of $NH_3$ and $SO_2$ aligned to the positionining of adjacent slits.

DETAILED DESCRIPTION OF THE INVENTION

Figure 1:
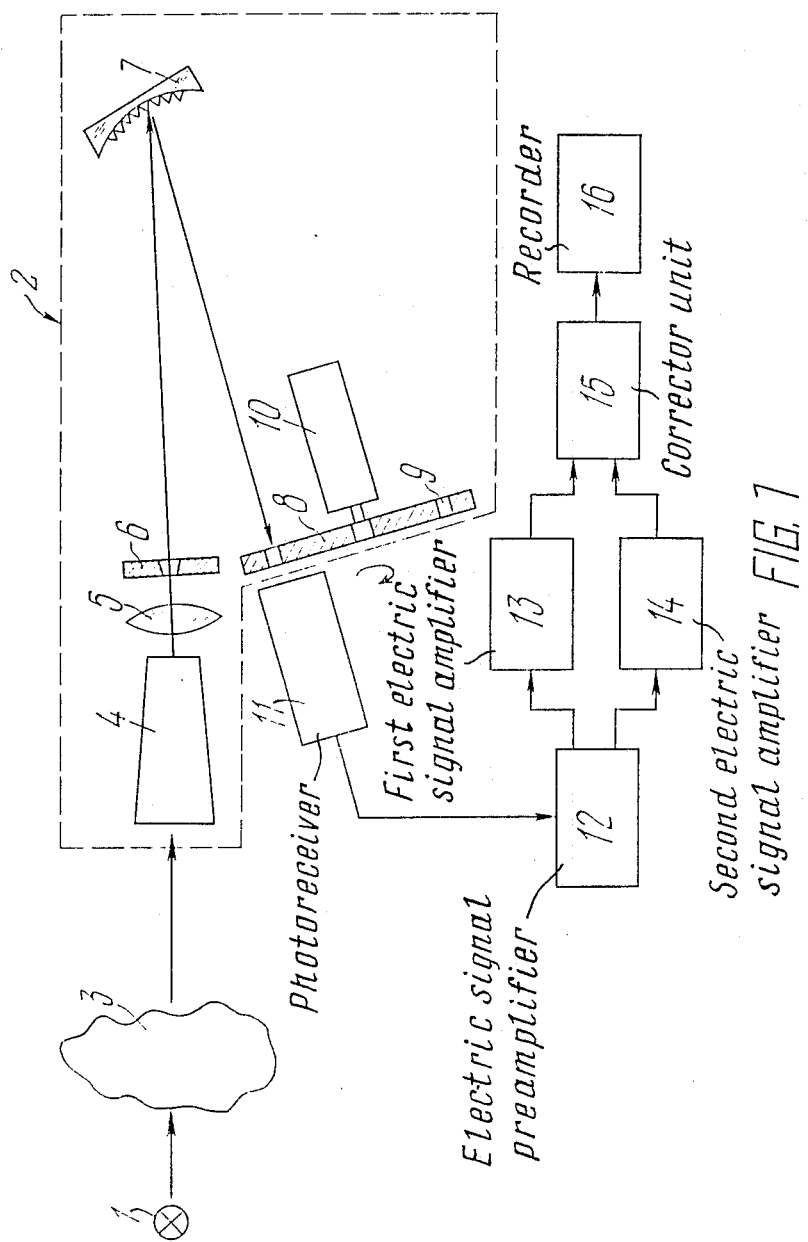

The correlational gas analyzer comprises light source 1 (FIG. 1) which can be an artificial or natural (Sun, Moon) source of light, and optical system 2. Gas 3 under study is positioned between light source 1 and optical system 2 and features a quasiperiodic pattern of the specified spectral band, and is contained in the atmosphere or in a special cell.

In this embodiment optical system 2 comprises sequentially positioned along the optical path blind 4 to exclude scattered light from the system, condensor 5 designed as a biconvex lens and focusing the light onto input slit iris 6, dispersing means 7 to decompose the specified spectral band, $\Delta\lambda$, of gas 3 under study designed as a convex grating, and rotatably mounted output slit iris 8. In other embodiments dispersing means 7 may be designed as a flat grating and a biconvex lens positioned downstream to focus the light beam onto output slit iris 8. In the embodiment being described output slit iris 8 is configured as a disc (in the following—disc 8) with a group of slits 9 uniformly distributed along its circumference and rotated by electric motor 10. Downstream of disc 8 is photoreceiver 11, with the output thereof connected to the inputs of electric signal amplifiers 13, 14 via electric signal preamplifier 12. Electric signal amplifier 13 is designed as a tuned amplifier, with the resonant frequency $f_1$ thereof defined by relation:

$$f_1 = (\Delta\lambda/\delta\lambda)/NK,$$

where $\Delta\lambda$ is the specified spectral band of gas 3 under study with a quasiperiodic pattern, $\delta\lambda$ is the period of the quasiperiodic pattern of specified spectral band $\Delta\lambda$ of gas 3 under study, N is disc 8 rotation speed, and K is the number of slits 9 in disc 8.

Electric signal amplifier 14 is designed as a tuned amplifier, with resonant frequency $f_2$ thereof differing from $f_1$ and defined by speed N of disc 8 rotation and by the number of slits 9 in disc 8; amplifier 14 serves to compensate instabilities of tuned amplifier 13 output signal, due to variations of light beam intensity.

In another embodiment a DC amplifier may be used as amplifier 14. The outputs of electric signal amplifiers 13, 14 are connected to the inputs of corrector unit 15, the output thereof is connected to recorder 16 calibrated in concentration units of gas 3 under study.

Figure 2:
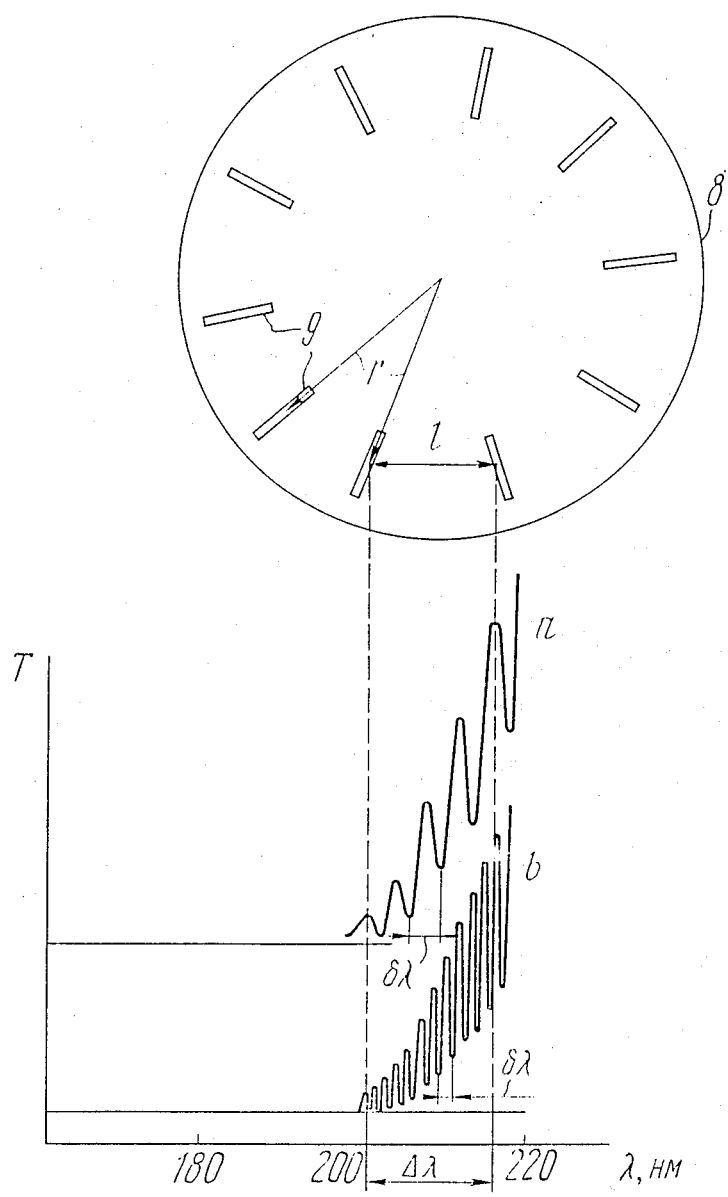

FIG. 2 shows disc 8 with a group of rectangular slits 9 (in the embodiment being described the number of slits 9 is 10) uniformly distributed along disc 8 circumference and equidistantly spaced by a distance r from disc 8 centre, with the spacing 1, between adjacent slits 9 centres approximately equal to the scan length in the scan plane (in the embodiment being described—the focal plane of the concave grating) of the specified spectral band, $\Delta\lambda$ of gas 3 under study. In case of dispersing means 7 decomposing specified spectral band $\Delta\lambda$ of gas 3 under study being designed as a flat grating and biconvex output lens, the non central spectral lines of gas 3 under study are bent, as is well known, and it becomes expedient to configure slits 9 in disc 8 as arcs of a circle positioned similarly to rectangular slits 9, so as to eliminate astigmatism of optical system 2.

For illustrativeness, the specified transmission bands of $NH_3$ and $SO_2$ (FIG. 2, curves a,b) are aligned in the drawing with the positions of slits 9 in disc 8.

The correlational gas analyzer according to this invention functions as follows.

The beam from light source 1 (FIG. 1) is passed through gas 3 under study and its spectrum acquires a typical quasiperiodic pattern in the specified spectral band, $\Delta\lambda$, as shown in FIG. 2. The beam is then passed via blind 4 to exclude scattered light and focused by condensor 5 onto input slit iris 6. After input slit iris 6 the beam arrives at a concave grating which decomposes the spectrum of the specified spectral band (FIG. 2) and focuses the decomposed spectrum in the concave grating's focal plane. Rotating disc 8 with a group of slits 9, positioned with a spacing 1 relative to one another, this spacing being equal to the scan length of specified spectral band $\Delta\lambda$ of gas 3 under study, acomplishes specified spectral band $\Delta\lambda$ continuous time scanning across photoreceiver 11 in such a way, that the end of scanning the specified spectral band by one slit 9 coincides with the start of scanning by the adjacent slit 9. Thus, during a single revolution of disc 8, specified spectral band $\Delta\lambda$ of gas 3 under study is scanned K times, where K is the number of slits 9 in disc 8. Photoreceiver 11 converts incident light into electric signals to drive preamplifier 12. The output signal of preamplifier 12 arrives at the inputs of electric signal amplifiers 13, 14, the former selecting and amplifying signals of $f_1$ frequency and suppressing signals of other frequencies. The transmission spectra shown in FIG. 2 for $NH_3$ (curve a) and $SO_2$ (curve b) feature a specified spectral band with a quasiperiodic pattern $\Delta\lambda$, of 200 nm to 215.5 nm and a period, $\delta\lambda$, of this quasiperiodic pattern of 3.8 nm and 1.6 nm, respectively. At a disk 8 rotation speed $N=60$ revolutions per second the resonant frequency, $f_1$, for $NH_3$ is 2400 Hz and for $SO_2$ is 6000 Hz.

Thus, to analyze $NH_3$ concentrations tuned amplifier 13 is tuned to 2400 Hz and to analyze $SO_2$ concentration—to 6000 Hz. During analysis the amplitude of the selected signal describes the concentration of gas 3 under study. In case of amplifier 14 being designed as a tuned amplifier, a signal of 600 Hz frequency is selected and amplified, this frequency characterizing the scanning process and being independent from the spectral characteristics of gas 3 under study, with signals of other frequencies being supressed as due to various interference. The output signals of amplifiers 13, 14 are applied to the inputs of corrector unit 15, wherein the amplitude of the $f_1$ frequency signal is reduced to that of the $f_2$ frequency signal, thus compensating variations in $f_1$ frequency signal amplitude due to changes in light intensity caused by non selective light absorption along the optical path and changes in light source 1 parameters. The result is an improved measurement accuracy. The reduced signal from the output of corrector unit 10 drives recorder 16, which displays the concentration of gas 3 under study in digital or analogue format.

If optical system 2 and light source 1 are housed in a common casing, this protecting the entire optical path from extraneous effects, it is preferrable to use a DC amplifier as amplifier 14 and reduce the amplitude of the $f_1$ frequency signal to the DC signal component. Further recording of the signal is acomplished as above.

Changeover to measurements of the content of another gas component of the multicomponent gas mixture involves only retuning of tuned amplifier 13 to a frequency $f_1$ corresponding to the $\Delta\lambda, \delta\lambda$ spectral characteristics of the gas 3 to be studied.

No replacements of disc 8 and its realignment in optical system 2 are required, this essentially improving the measurement accuracy.

Thus, the correlational gas analyzer of the invention is characterized by low production cost and simplicity of optical system alignment and use.

What is claimed is:

1. A correlational gas analyzer, comprising:
   a light source, with the beam thereof passed through the gas under study, this gas featuring a quasiperiodic pattern of the specified spectral band characterized by the number of maxima or minima and the pattern period;
   an optical system positioned downstream of the gas under study with a quasiperiodic pattern of the specified spectral band and comprising sequentially positioned along the optical path:
   condensor;
   input slit iris;
   dispersing means for decomposing the specified spectral band of the gas under study;
   output slit iris, mounted rotatably and configured as a disc with a plurality of slits for scanning the specified spectral band of the gas under study and uniformly distributed along the disc circumference and equidistantly spaced from the disc center, with the spacing between the centers of adjacent slits approximately equal to the scan length in the scan plane of the specified spectral band of the gas under study, this scan plane being the focal plane of the said dispersing means of the specified spectral band of the gas under study;
   a photoreceiver to receive the beam after passage of the said output slit iris;
   a first electric signal amplifier with input connected to the output of said photoreceiver and designed as a tuned amplifier with the resonant frequency thereof defined by a preset relation between the disc rotation speed, the number of maxima or minima in the specified spectral band of the gas under study, and the number of slits in the plurality of slits;
   a second electric signal amplifier with input connected to the output of said photoreceiver;
   a corrector unit with input connected to the outputs of said first and said second electric signal amplifier;
   a recorder with input connected to the output of said corrector unit.

2. A correlational gas analyzer as substantially set forth in claim 1, wherein the said resonant frequency $f_1$ of said first electric signal amplifier defined by equation $f_1 = (\Delta\lambda/\delta\lambda) NK$, where $\Delta\lambda$ is the specified spectral band of the gas under study, $\delta\lambda$ is the pattern period of the specified spectral band of the gas under study, N is the disc rotation speed, and K is the number of slits in the plurality of slits.

3. A correlational gas analyzer as substantially set forth in claim 1, wherein said second electric signal amplifier is a tuned amplifier with the resonant frequency thereof defined by the disc rotation speed and the number of slits in the plurality of slits.

4. A correlational gas analyzer as substantially set forth in claim 2, wherein said second electric signal amplifier is a tuned amplifier with the resonant frequency thereof defined by the disc rotation and the number of slits in the plurality of slits.

* * * * *